United States Patent [19]

Toth

[11] Patent Number: 5,400,378
[45] Date of Patent: Mar. 21, 1995

[54] DYNAMIC DOSE CONTROL IN MULTI-SLICE CT SCAN

[75] Inventor: Thomas L. Toth, Brookfield, Wis.

[73] Assignee: General Electric Company, Milwaukee, Wis.

[21] Appl. No.: 155,045

[22] Filed: Nov. 19, 1993

[51] Int. Cl.⁶ .............................................. A61B 6/00
[52] U.S. Cl. ....................................... 378/16; 378/108; 378/110
[58] Field of Search ................... 378/4, 8, 16, 20, 108, 378/109, 110, 98

[56] References Cited

U.S. PATENT DOCUMENTS 4,624,007 11/1986 Muranushi .............................. 378/4
5,103,469 4/1992 Tanaka ............................... 378/20 X Primary Examiner—David P. Porta
Attorney, Agent, or Firm—Quarles & Brady

[57] ABSTRACT

An x-ray CT system performs a multi-slice scan in which tube current is modulated to reduce the x-ray dose without increasing image noise. Scout data is acquired from which a relative attenuation function (RAF) is calculated to relate expected patient attenuation of the x-ray beam at each slice to a reference. Tube current commands (mA) for each slice are calculated from the RAF and used to acquire image data.

8 Claims, 3 Drawing Sheets

DYNAMIC DOSE CONTROL IN MULTI-SLICE CT SCAN

BACKGROUND OF THE INVENTION

The present invention relates to computed tomography (CT) imaging apparatus; and more particularly, to reducing the x-ray dose applied to a patient without significantly increasing noise artifacts in the image.

In a current computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a cathode ray tube display. In a typical CT scan, data is acquired from which a set of 2D images taken through contiguous slices may be reconstructed. In such scans, the patient table may be moved after each revolution of the gantry to acquire attenuation data for the next slice. In the alternative, a so-called helical scan may be performed in which the table is slowly moved as the gantry is revolved to acquire all the slices in one continuous motion.

Quantum noise degrades the diagnostic quality of a CT image and this noise is related to the amount of x-rays, or "dose", employed to acquire the attenuation measurements, and to the attenuation characteristics of the patient. Image artifacts due to noise will increase if the x-rays measured at the detectors drop to low levels either because the prescribed x-ray dose is too low or the beam is highly attenuated by patient anatomy. The x-ray dose is controlled by the filament current ("mA") applied to the x-ray tube, and the practice is to fix this current at a level which provides a constant dose during the entire scan. If the operator prescribes a high dose, image quality is superb throughout, but excessive x-ray flux is produced during portions of the scan when patient attenuation is low. The patient is thus exposed to an excessive dose and the x-ray tube is unnecessarily heated. On the other hand, if the dose is reduced (to prevent tube overheating during the prescribed scan), noise artifacts will appear in the image at locations where the beam is highly attenuated, in the hips or shoulders, for example. Technologists try to deal with these variables to optimize the prescribed dose by visually estimating parameters for a given patient.

SUMMARY OF THE INVENTION

The present invention relates to an x-ray CT system in which the dose applied to the patient during a scan comprised of a series of slice acquisitions is modulated from slice-to-slice. More specifically, patient projection data is acquired from each slice to be acquired, and this data is employed to calculate the x-ray tube current applied during the subsequent acquisition of each slice to modulate patient dose while maintaining a selected scan performance specification. In one embodiment of the invention, image quality associated with a reference object is specified and a relative attenuation function ("RAF") is calculated from the patient projection data which relates expected patient image quality to that of the reference object for each slice. The RAF may be used to modulate a reference tube current ($mA_{ref}$) for each slice of the scan, where $mA_{ref}$ is selected to provide the desired image quality (i.e. noise level) in the reference object.

A general object of the invention is to reduce patient dose during a multi-slice CT scan without significantly degrading image quality relative to a known reference. Tube current (mA) for each slice is automatically calculated by multiplying the RAF at the slice times the selected reference current ($ma_{ref}$) and normalizing the result by the ratio of the reference image technics (i.e. kv, slice thickness, and scan time) and the prescribed exam technics. During the subsequent exam, tube current will be reduced below the reference value ($ma_{ref}$) at slice locations of minimal patient attenuation, thus reducing overall patient dose.

Another object of the invention is to enable the operator to reduce patient dose by specifying different image quality requirements over regions of the RAF. For example, high resolution studies of high contrast anatomy can tolerate higher noise levels than the selected reference level. Accordingly, the operator may divide the slices spanned by the RAF into regions in which "high", "medium" or "low" noise performance is desired. The reference current ($mA_{ref}$) used to calculate the tube current (mA) for each slice is scaled down to provide high noise performance and is scaled up to provide low noise performance in the respective regions.

Another specific object of the invention is to reduce x-ray tube overheating during a CT scan. Instead of computing the mA relative to a known noise reference, the CT technologist may elect to explicitly select the x-ray technic based on criteria with which he is currently familiar. Before the scan series is executed, a tube cooling algorithm (as it is known to those skilled in the art) computes if the tube heating capacity will be exceeded. If tube heat capacity will be exceeded, the user must decide where and by how much to reduce the mA or otherwise change the examination prescription in order to complete the examination without a tube overheating interruption. In accordance with the principles of this invention, the RAF can be used to automatically lower the user specified mA at those locations which require less dose in order to satisfy the tube cooling algorithm and thereby allow the examination to be executed without tube overheating or a clinically significant image noise penalty.

Yet another specific object of the invention is to detect potential detector overranging conditions. The dynamic range of the detector system is designed for optimum performance in the range where most patient signals occur. At times the x-ray signal can be so intense that an overrange condition can result. This can happen, for example, if the patient is not properly centered in the field of view. An overrange condition can produce undesired artifacts in the image. The patient projection data can be used to determine if the prescribed exam will produce signals high enough to cause an overrange, and if so, the operator can be alerted to the condition or tube current can automatically be scaled down to an acceptable level.

Yet another specific object of the invention is to predict when objectionable levels of non-quantum noise will occur in the prescribed patient images. Noise in patient images generally is due to quantum noise which is governed by x-ray photon statistics. However, internal noise sources within the DAS and detector add in quadrature with the x-ray quantum noise. When x-ray signal levels are low the electrical signals are also low and small noise sources within can become a significant part of the total noise on the detected signal. Non-quantum noise is generally observable in an image when the ratio of total noise on the signal to quantum noise is greater than 1.1. The signal levels at which this occurs can be predetermined for a given DAS and detector design. The patient projection data can be used to determine if the prescribed exam will produce signals below this limit even at maximum tube current, and if so, the operator can be alerted to the condition or the exam technic factors (kV or Slice Thickness) can be increased to improve the quality of the patient image.

DETAILED DESCRIPTION OF THE INVENTION

Figure 1:
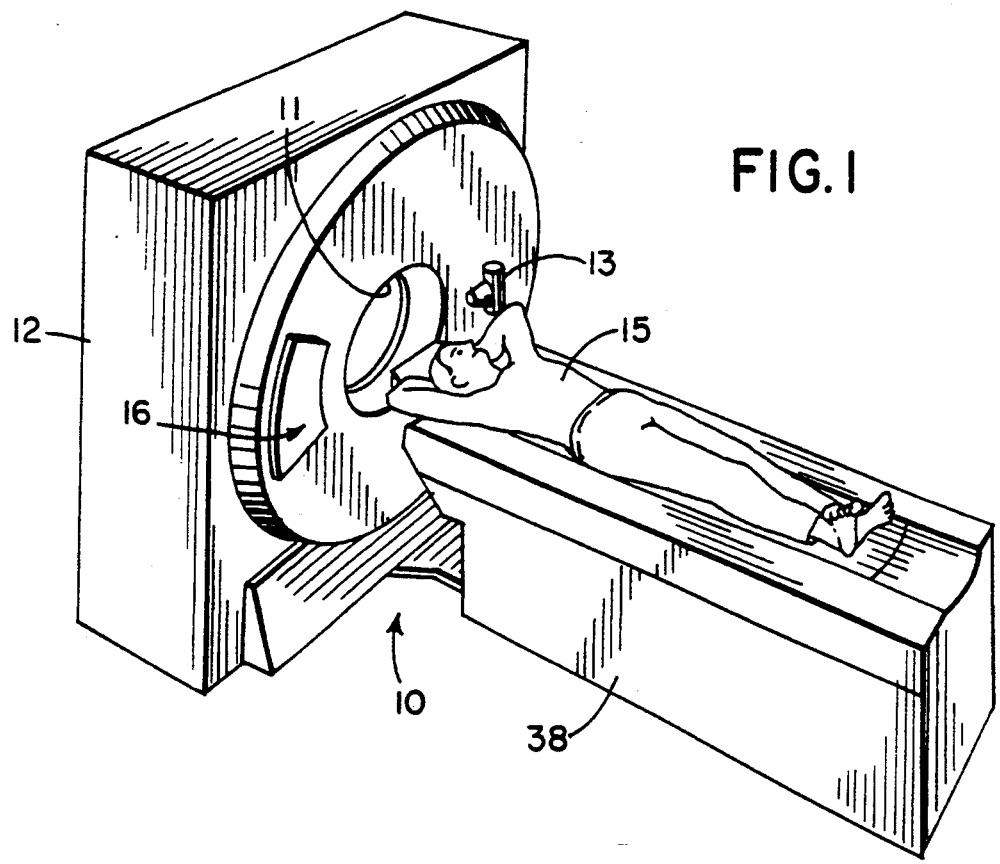
FIG. 1 is a pictorial view of a CT imaging system in which the present invention may be employed.
Figure 2:
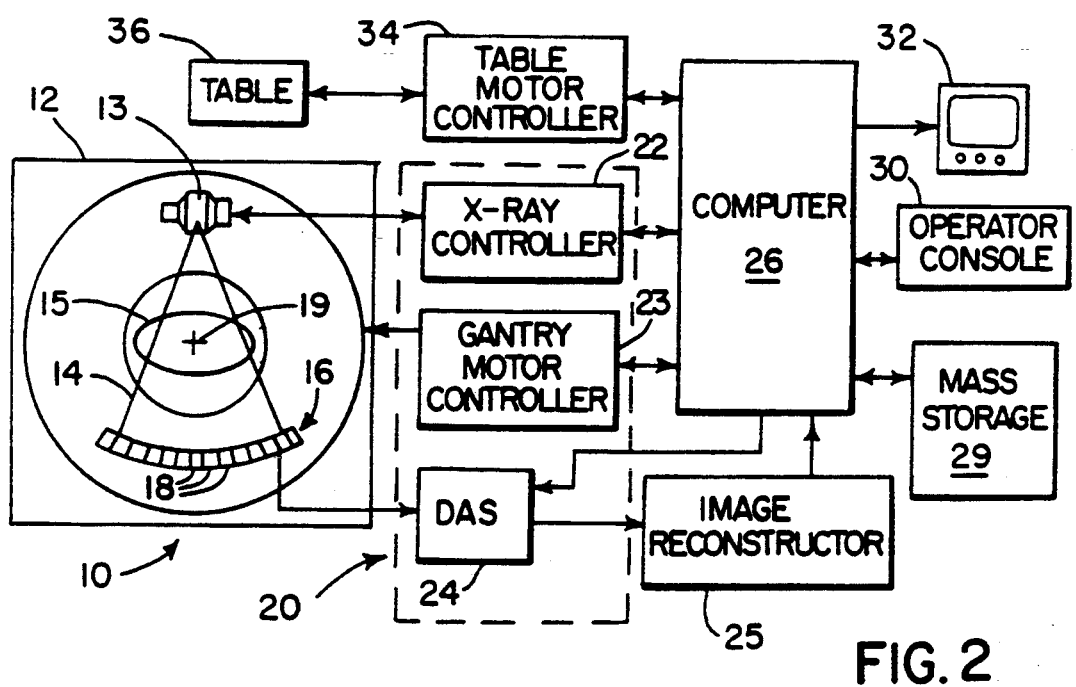
FIG. 2 is a block schematic diagram of the CT imaging system.

With initial reference to FIGS. 1 and 2, a computed tomography (CT) imaging system 10 includes a gantry 12 representative of a "third generation" CT scanner. Gantry 12 has an x-ray source 13 that projects a beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15. A reference detector at one end of the array 16 measures the unattenuated beam intensity during the scan to detect variations in the applied x-ray dose. This reference data is used in subsequent processing of the x-ray projection data to normalize it to a common reference dose.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction. The reconstructed image is applied as an input to a computer 26 which stores the image in a mass storage device 29.

The computer 26 also receives commands and scanning parameters from an operator via console 30 that has a keyboard. An associated cathode ray tube display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12.

Figure 3:
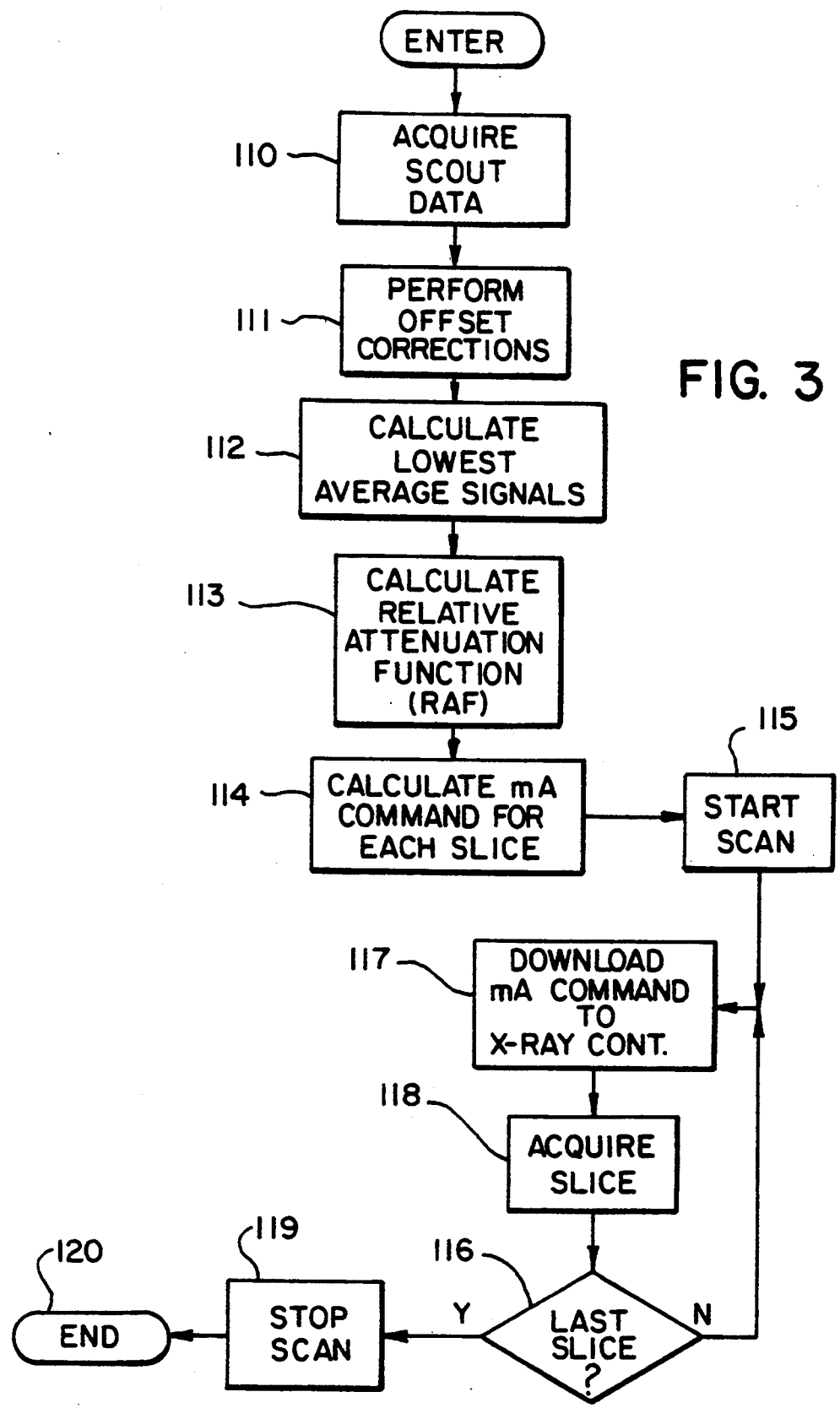
FIG. 3 is a flow chart of a program executed by the CT imaging system of FIG. 2 to carry out the preferred embodiment of the invention.
Figure 4:
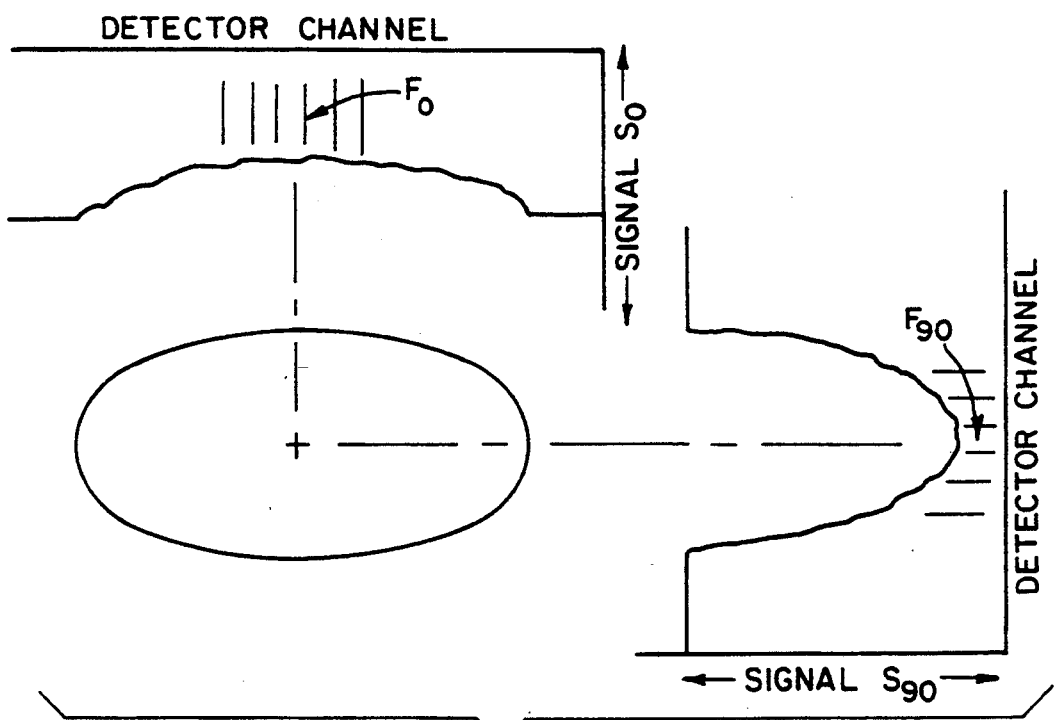
FIG. 4 is a graphic representation of attenuation data obtained from a patient during a scout scan.

Referring particularly to FIG. 2, the computer 26 directs the system components to carry out the prescribed scan in accordance with stored programs. The program illustrated by the flow chart in FIG. 3 is executed by computer 26 to implement the preferred embodiment of the present invention. The first step is to acquire scout data, as indicated at process block 110. As illustrated in FIG. 4, this scout data is comprised of two orthogonal views from each slice in the prescribed scan, one at a gantry angle of 0° and the other at an angle of 90°.

Figure 5:
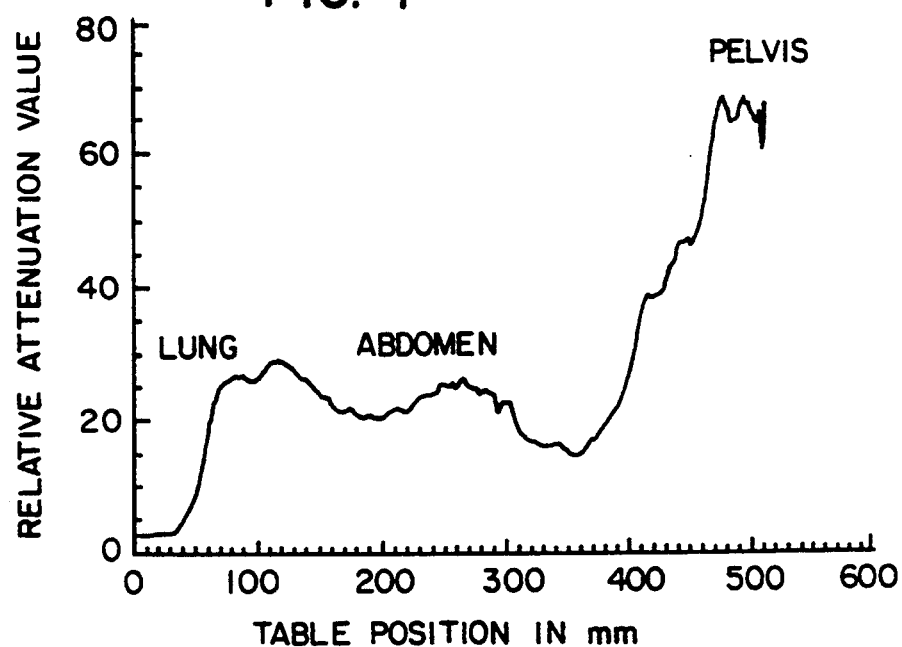
FIG. 5 is a graphic representation of a relative attenuation function produced in accordance with the present invention.

As indicated at process block 111, the usual offset corrections are made to the acquired scout data $S_0(i,z)$ and $S_{90}(i,z)$, and the lowest average signal within one of five groups of 70 channels for each orthogonal projection are computed at process block 112 to provide two signals $F_0(z)$ and $F_{90}(z)$ for each slice in the scan as shown in FIG. 4. The five groups of 70 channels are centered on the isocenter and span a range sufficient to measure the maximum attenuation even when the patient is not perfectly centered. For each slice, a relative attenuation value $RAF(z)$ is calculated as indicated at process block 113, and together these define a relative attenuation function which indicates the x-ray attenuation expected at each slice in the scan. If graphed on a display, for example, the relative attenuation function might appear as shown in FIG. 5. The relative attenuation values may be determined using a number of methods which will be described in more detail below. Also, the patient projection data is acquired using a scout scan in the preferred embodiment, but this data could also be acquired in a helical survey scan or from adjacent slice data acquired during a prior acquisition.

Referring again to FIG. 3, the next step in the process is to calculate tube current commands mA for each slice in the scan using the RAF values, as indicated at process block 114. There are a number of methods for accomplishing this calculation which will be described in more detail below. These methods may also use the RAF values to predict possible problems during the scan, such as exceeding the current limits of the x-ray controller 22, overheating the x-ray tube, or overranging the DAS channels. The system is then prepared to perform the scan which is started at process block 115.

Once the scan is started, the system remains in a loop until the last slice has been acquired, as determined at decision block 116. For each slice, the computer 26 downloads the calculated current command mA to the x-ray controller 22 at process block 117, and directs the control mechanism 20 to acquire the attenuation data for one slice as indicated at process block 118. This cycle is repeated for each slice in the scan with the x-ray dose for each slice being governed by the calculated current command mA for the slice. Referring to FIG. 5, for example, for slices acquired through the patient's lungs the current command will be relatively low, whereas it will be high for slices through the patient's hips. By employing the present invention, image quality will be consistent throughout the scan. When the last slice has been acquired, the scan is stopped as indicated at process block 119 and the program exits at 120.

As indicated above, the RAF function can be calculated in a number of ways from the two orthoganal patient signals $F_0(z)$ and $F_{90}(z)$. The data may be related to that of a known phantom in a first method by first selecting the lower of the two orthogonal signals for each slice:

$$S_{min}(z) = \text{minimum of } F_0(z) \text{ or } F_{90}(z).$$

This minimum signal acquired during the scout scan ("sc") is normalized relative to a set of standard ("std") exposure parameters, or "technics":

$$S_n(z) = S_{min}(z)(kV_{std}/kV_{sc})^2 \frac{mA_{std} thk_{std} time_{std}}{mA_{sc} thk_{sc} time_{sc}}.$$

The ratio of a signal produced at the standard technics by a known phantom is then calculated:

$$raf(z) = S_{std}/S_n(z),$$

and the resulting set of data is low pass filtered using a 5 mm wide boxcar filter F(z):

$$RAF(z) = F(z)*raf(z).$$

The resulting relative attenuation function represents the attenuation of the patient relative to a known phantom and a known technic. This enables technologists to more easily relate the expected image quality of the patient to a known reference object.

An alternative method for calculating the relative attenuation function uses orthogonal reconstructed scout images that have first been added to a scout bowtie image. A scout bowtie image is the scout image that would be displayed if an image of the bowtie attenuation were generated without a display offset. The maximum value is selected from the average of five regions of 50 pixels each within a strip of pixels for a slice from the orthogonal scout images plus a scout bowtie image.

$$I_c(z) = \text{maximum of } I_0(r,z) \text{ and } I_{90}(r,z) \text{ where}$$
$$r = \text{regions 1 to 5}$$

The difference between this maximum image value ($I_c(z)$) and the maximum scout image value ($I_{std}$) computed in the same manner from a known phantom (such as a 20 cm water phantom) is calculated:

$$I_{raf}(z) = I_{std} - I_c(z)$$

This is divided by the system scale factor ($K_{sys}$) and the result is exponentiated to obtain the relative attenuation function.

$$raf(z) = e^{I_{ref}/k_{sys}}$$

As in the first method described above, this array of data is low pass filtered using a 5 mm wide boxcar filter F(z) to provide the final relative attenuation function:

$$RAF(z) = F(z)*raf(z).$$

The calculation of the current commands (mA) from the RAF (z) values can be as simple as scaling RAF(z) to a reference current $mA_{ref}$:

$$mA(z) = mA_{ref}(RAF(z)/RAF_{ref})$$

If the technics are different for the exam, the values must also be normalized as follows:

$$mA(z) = mA_{ref}(RAF(z)/RAF_{ref})(kV_{std}/kV_{ex})^2(thk_{std} time_{std}/thk_{ex} time_{ex}).$$

The resulting current commands are checked to insure none exceed the upper or lower limits of the x-ray controller 22. If any do, they can be set to the controller limit or the operator may be signaled. The scout data may also be used to determine if any signals during the scan will be insufficient in magnitude at the designated technics, or will be too large and will overrange the detector channels.

To test if the signal for a slice will exceed the upper limit and thereby cause an overrange condition, the maximum channel signal level in the offset correct orthogonal patient projections is found:

$$S_{max}(Z) = \text{maximum value in } S_0(i,z) \text{ and } S_{90}(i,z)$$

This maximum value is scaled by the exam technic factors, its offset correction value is restored (added) and the result is compared to the upper limit:

upper
limit $> S_{max}(Z)(kV_{ex}/kV_{sc})^2(mA_{ex} thk_{ex})/(mA_{sc} thk_{sc}) + \text{offset}_{max-ch}$ If the result is greater than the upper limit, the mA would be reduced and/or the technologist would be notified. The upper limit is the maximum signal that the DAS can measure minus some design margin.

To test if the signal for a slice is too low, even with maximum mA, at user selected technic, the minimum average patient signal region ($S_{min}(z)$) is scaled by the exam technic factors and compared to the minimum limit:

minimum
limit $< S_{min}(z)(kV_{ex}/kV_{sc})^2(mA_{ex} thk_{ex})/(mA_{sc} thk_{sc})$ If the signal is less than the minimum limit, the user is notified that a significant image quality noise improvement can be achieved if the exam kV and/or slice thickness are increased. The minimum limit is a predetermined point where the ratio of total noise in the raw signal relative to the quantum noise in the raw signal is greater than 1.1.

Also, x-ray tube heating can be predicted based on the current commands (mA) and the examination technics. If problems are found, the technics or mA commands can be changed for those slices where the signal (dose) is highest before the scan is performed.

It should be apparent to those skilled in the art that variations from the preferred embodiments described above can be made without departing from the spirit of the invention. For example, the invention may be applied to a conventional scan in which each slice is acquired while the patient table 36 is stationary, or it may be employed in a helical scan in which the patient table 36 is moved slowly at a constant rate during the acquisition of all slices.

I claim:

1. A method for adjusting the dose of an x-ray beam applied to a patient by an x-ray CT system during a multi-slice acquisition of attenuation data, the steps comprising:

acquiring patient projection data from each slice which indicates patient attenuation of the x-ray beam;

calculating a relative attenuation function RAF(z) from the acquired patient projection data which indicates the expected x-ray beam attenuation at each slice location relative to the x-ray beam attenuation of a known reference object;

calculating an x-ray tube current command mA(z) for each slice using the corresponding value of the relative attenuation function RAF(z) and a reference x-ray tube current command $mA_{ref}$ which produces the desired x-ray dose in the known reference object; and acquiring each slice of attenuation data with an x-ray dose determined by the x-ray tube current command mA(z) for that slice.

2. The method as recited in claim 1 in which the attenuation of the known reference object is acquired at a standard technic and the patient projection data is normalized to the standard technic.

3. The method as recited in claim 2 in which the calculated x-ray tube current commands are normalized to the standard technic.

4. The method as recited in claim 1 in which the relative attenuation function RAF(z) is calculated as the ratio of the patient attenuation data to the attenuation produced by the known reference object.

5. The method as recited in claim 4 in which the patient projection data from each slice is comprised of attenuation data acquired at two orthogonal gantry angles, and the patient attenuation data used to calculate the relative attenuation function RAF(z) at each slice is that patient projection data which is greater.

6. The method as recited in claim 1 in which the patient projection data is acquired in a scout scan from each slice comprised of attenuation data acquired at two orthogonal gantry angles.

7. The method as recited in claim 1 in which the patient attenuation data is employed to detect an overranging condition at a slice and the x-ray tube current command mA(z) for that slice is reduced.

8. The method as recited in claim 1 in which the patient attenuation data is employed to detect a high non-quantum noise condition at a slice and the x-ray tube current command mA(z) for that slice is increased.

* * * * *